United States Patent
Cheatham, III et al.

(10) Patent No.: US 10,537,262 B2
(45) Date of Patent: Jan. 21, 2020

(54) SYSTEMS AND METHODS FOR DETECTING STROKES

(71) Applicants: Elwha LLC, Bellevue, WA (US); Jacqueline S. Deerr-Lord, Seattle, WA (US); Julie G. Lord, Federal Way, WA (US)

(72) Inventors: Jesse R. Cheatham, III, Seattle, WA (US); Matthew G. Dyor, Bellevue, WA (US); Peter N. Glaskowsky, Carnation, WA (US); Kimberly D. A. Hallman, Bellevue, WA (US); Roderick A. Hyde, Redmond, WA (US); Muriel Y. Ishikawa, Livermore, CA (US); Edward K. Y. Jung, Bellevue, WA (US); Michael F. Koenig, Bellevue, WA (US); Richard T. Lord; Robert W. Lord, Seattle, WA (US); Craig J. Mundie, Seattle, WA (US); Nathan P. Myhrvold, Medina, WA (US); Robert C. Petroski, Seattle, WA (US); Desney S. Tan, Kirkland, WA (US); Lowell L. Wood, Jr., Bellevue, WA (US)

(73) Assignee: ELWHA LLC, Bellevue, WA (US)

( * ) Notice: Subject to any disclaimer, the term of this patent is extended or adjusted under 35 U.S.C. 154(b) by 508 days.

(21) Appl. No.: 14/712,640

(22) Filed: May 14, 2015

(65) Prior Publication Data
US 2016/0331255 A1    Nov. 17, 2016

(51) Int. Cl.
*A61B 5/046*    (2006.01)
*A61B 5/03*    (2006.01)
*A61B 5/11*    (2006.01)

(52) U.S. Cl.
CPC .............. *A61B 5/046* (2013.01); *A61B 5/031* (2013.01); *A61B 5/1116* (2013.01)

(58) Field of Classification Search
None
See application file for complete search history.

(56) References Cited

U.S. PATENT DOCUMENTS

| 6,705,990 B1 | 3/2004 | Gallant et al. |
| 7,558,622 B2 | 7/2009 | Tran |

(Continued)

OTHER PUBLICATIONS

Andrade et al., "Detection of occult atrial fibrillation in patients with embolic stroke of uncertain source: a work in progress". Frontiers in Physiology, Apr. 25, vol. 6, Article 100, pp. 1-9.*

(Continued)

*Primary Examiner* — Katherine L Fernandez
*Assistant Examiner* — Yi-Shan Yang
(74) *Attorney, Agent, or Firm* — Foley & Lardner LLP

(57) ABSTRACT

A system for detecting a type of stroke includes a processing circuit. The processing circuit is configured to receive heart data regarding a heart rhythm of a patient and physiological data regarding a physiological characteristic of the patient. The heart data is indicative of an occurrence of atrial fibrillation and the physiological data is indicative of an occurrence of a stroke. The processing circuit is further configured to determine a likelihood that the stroke was an embolic stroke based on the heart data and to provide an output including an indication of the likelihood that the stroke was an embolic stroke.

24 Claims, 6 Drawing Sheets

(56) References Cited

U.S. PATENT DOCUMENTS

| | | | |
|---|---|---|---|
| 8,108,036 B2 | 1/2012 | Tran | |
| 2007/0276270 A1 | 11/2007 | Tran | |
| 2009/0318779 A1 | 12/2009 | Tran | |
| 2010/0145164 A1* | 6/2010 | Howell | A61B 5/0002 600/301 |
| 2010/0217100 A1* | 8/2010 | LeBoeuf | A61B 5/00 600/301 |
| 2012/0158074 A1 | 6/2012 | Hall | |
| 2014/0172310 A1* | 6/2014 | Chin | G06F 19/3406 702/19 |

OTHER PUBLICATIONS

Brambatti et al, "Temporal Relationship Between Subclinical Atrial Fibrillation and Embolic Events" Circulation. 2014, 129, pp. 2094-2099.*

Healey et al, "Subclinical Atrial Fibrillation and the Risk of Stroke" New Eng. J. Med. 2012, 366:2, pp. 120-129.*

Arboix et al, "Cardioembolic Stroke: Clinical features, Specific Cardiac Disorders and Prognosis" Current Cardiology Reviews, 2010, 6, 150-161.*

Gladstone et al., "Atrial Fibrillation in Patients with Cryptogenic Stroke". The New England Journal of Medicine. 2014, vol. 370, No. 26, pp. 2467-2477.*

Lorenzo Scalise (2012). Non Contact Heart Monitoring, Advances in Electrocardiograms—Methods and Analysis, PhD. Richard Millis (Ed.), In Tech.*

* cited by examiner

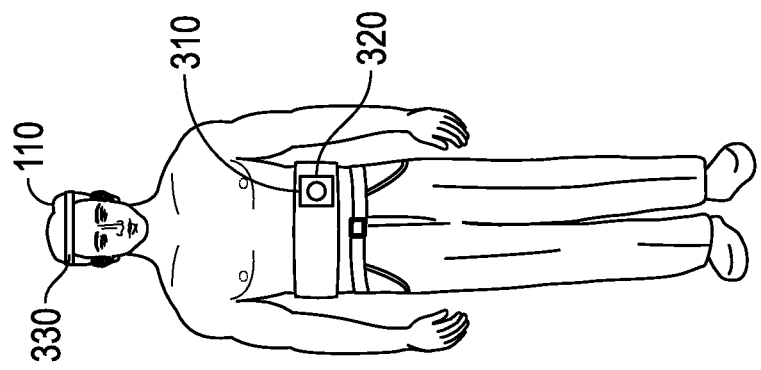
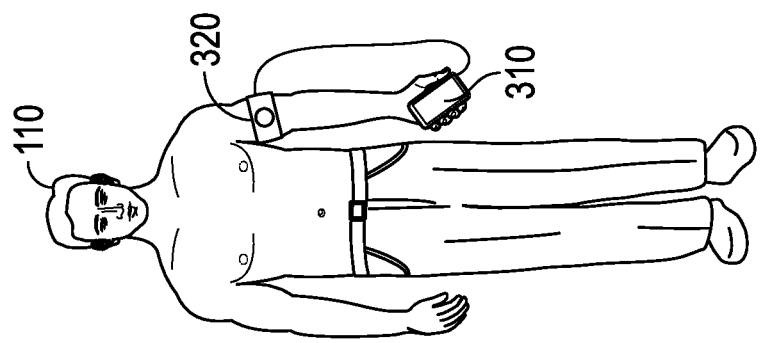
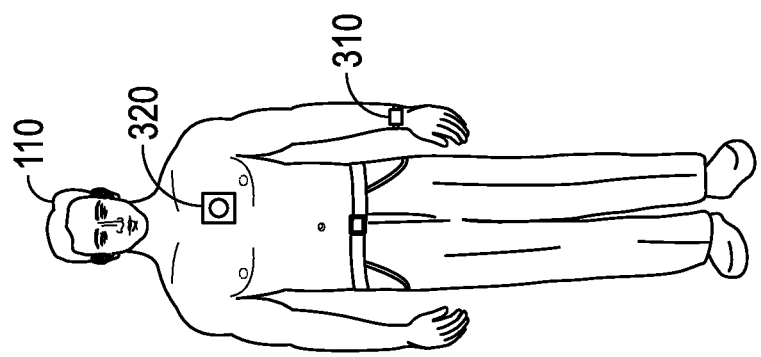

SYSTEMS AND METHODS FOR DETECTING STROKES

BACKGROUND

A stroke is the disturbance in blood supply to the brain. Two major categories of strokes are ischemic strokes and hemorrhagic strokes. Ischemic strokes are caused when blood supply to part of the brain is decreased, thereby depriving the brain of oxygen and destroying brain tissue. Ischemic strokes may be caused by thrombosis (obstruction of a blood vessel by a blood clot forming in the blood vessel), embolism (obstruction of a blood vessel by an embolus traveling from elsewhere in the body, also known as an "embolic stroke"), systematic hypoperfusion (general decrease in blood supply, e.g., due to shock), venous thrombosis (obstruction of a blood vessel in the sinuses which drains blood from the brain). Hemorrhagic strokes are caused by a ruptured artery in the brain, which causes blood to pool and destroy brain tissue. Both ischemic and hemorrhagic strokes may cause severe deficits in a patient, therefore a patient that has experienced a stroke should seek medical treatment as soon as possible. Other medical conditions, such as atrial fibrillation, may cause a patient to be particularly susceptible to certain stroke types, such as embolic strokes.

Due to the different etiologies of ischemic and hemorrhagic strokes, each stroke type requires different treatment plans. For example, strokes caused by clotting (e.g., thrombolytic and embolic strokes) may be treated with a "clot busting" medication that should be administered within the first three hours of the onset of a stroke. When a stroke is properly treated, a patient's mental and physical deficits may be minimized. Misguided treatment plan (e.g., upon misdiagnosing a stroke) could progress the stroke and possibly lead to death.

SUMMARY

One embodiment relates to a system for detecting a type of stroke that includes a processing circuit. The processing circuit is configured to receive heart data regarding a heart rhythm of a patient and physiological data regarding a physiological characteristic of the patient. The heart data is indicative of an occurrence of atrial fibrillation and the physiological data is indicative of an occurrence of a stroke. The processing circuit is further configured to determine a likelihood that the stroke was an embolic stroke based on the heart data and to provide an output including an indication of the likelihood that the stroke was an embolic stroke.

Another embodiment relates to a method for detecting a type of stroke. The method includes receiving heart data regarding a heart rhythm of the patient and receiving physiological data regarding a physiological characteristic of the patient. The physiological data is indicative of an occurrence of a stroke and the heart data is indicative of an occurrence of atrial fibrillation prior to the stroke. The method further includes determining a likelihood that the stroke was an embolic stroke based on the heart data.

Another embodiment relates to a system for detecting a type of stroke that includes a heart-monitoring device and a processing circuit. The heart-monitoring device is configured to acquire heart data regarding a heart rhythm of a patient. The heart data is indicative of an occurrence of atrial fibrillation and the heart-monitoring device acquires heart data using micro impulse radar. The processing circuit is configured to receive the heart data and physiological data. The physiological data regards a physiological characteristic of the patient and is indicative of the occurrence of a stroke. The processing circuit is further configured to determine a likelihood that the stroke was an embolic stroke based on the physiological data and the heart data, and to control operation of an output device to provide the output, wherein the output is based on the likelihood that the stroke was an embolic stroke.

Another embodiment relates to a method for detecting a stroke. The method includes receiving heart data regarding a heart rhythm of a patient and receiving physiological data regarding a physiological characteristic of the patient. The heart data is indicative of an occurrence of atrial fibrillation and the physiological data is indicative of an occurrence of a stroke after the occurrence of the atrial fibrillation. The method further includes determining a likelihood that the stroke was an embolic stroke based on the physiological data and the heart data, and providing an output, wherein the output is based on the likelihood that the stroke was an embolic stroke.

Another embodiment relates to a device for detecting a stroke that includes a heart-monitoring sensor, a physiological sensor, and a stroke detection module. The heart-monitoring sensor is configured to monitor a heart rhythm of a patient, and monitoring the heart rhythm includes acquiring heart data. The physiological sensor is configured to monitor a physiological characteristic of the patient, and monitoring the physiological characteristic includes acquiring physiological data. The stroke detection module includes a processing circuit configured to determine whether the patient experienced a stroke based on the monitored physiological characteristic; determine whether the patient experienced atrial fibrillation based on the monitored heart rhythm; determine whether the patient experienced an embolic stroke based on the patient experiencing a stroke and atrial fibrillation within a predetermined time period; and control operation of the device to provide an output, wherein the output is based on the determination of whether the patient experienced an embolic stroke.

Another embodiment relates to a method for detecting a medical event. The method includes monitoring a heart rhythm of a patient and monitoring a physiological characteristic of the patient. Monitoring the heart rhythm includes acquiring heart data and monitoring the physiological characteristic includes acquiring physiological data. The method further includes determining whether the patient experienced a stroke based on the monitored physiological characteristic; determining whether the patient experienced atrial fibrillation based on the monitored heart rhythm; determining whether the patient experienced an embolic stroke based on the patient experiencing a stroke and atrial fibrillation within a predetermined time period; and providing an output, including whether the patient experienced an embolic stroke.

Another embodiment relates to a system for determining a probability of a patient experiencing a stroke that includes a heart-monitoring sensor and a processing circuit. The heart-monitoring sensor is configured to monitor a heart rhythm of the patient. The processing circuit is configured to receive heart data from the heart-monitoring sensor, wherein the heart data is based on the monitored heart rhythm, and wherein the heart data is indicative of whether the patient experiencing atrial fibrillation; determine a probability of the patient experiencing a future stroke based on the heart data; and provide an output based on the probability of the patient experiencing a future stroke.

Another embodiment of the invention relates to a method for determining a probability of a patient experiencing a stroke. The method includes receiving heart data, wherein the heart data is based on a monitored heart rhythm, and wherein the heart data is indicative of the patient experiencing atrial fibrillation; determining a probability of the patient experiencing a future stroke based on the heart data; and providing an output based on the probability of the patient experiencing a future stroke.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIG. 3A is an illustration of a wearable stroke detection device, according to one embodiment.

FIG. 3B is an illustration of a wearable stroke detection device, according to another embodiment.

FIG. 3C is an illustration of a wearable stroke detection device, according to another embodiment.

DETAILED DESCRIPTION

Figure 1:
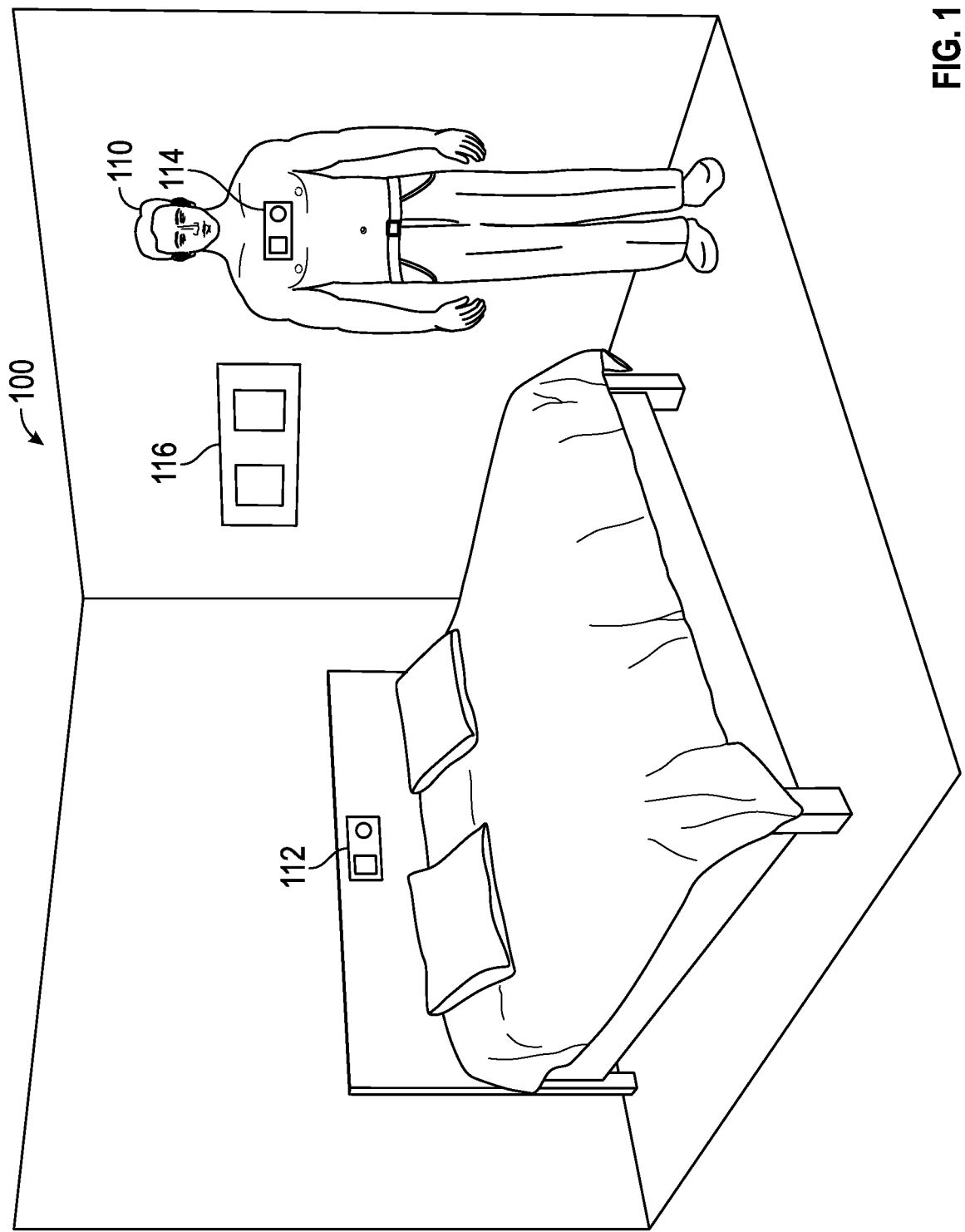
FIG. 1 is an illustration of a home system for detecting a stroke, according to one embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the scope of the subject matter presented here.

Referring generally to the figures, various embodiments of systems, methods, and computer readable media for detecting strokes are shown and described. Strokes remain one of the leading causes of death in the world. Furthermore, as people age, the likelihood of experiencing a stroke increases. Heart fibrillation (e.g., proximal atrial fibrillation) is a common precursor of certain types of strokes. For example, an embolic stroke is often preceded by atrial fibrillation. In some cases, atrial fibrillation may occur one-half to three hours before an emboli is ejected from the left ventricle of a person's heart and, in some cases, travels to the brain, thereby blocking a blood vessel in the brain and causing a thrombotic (or embolic) stroke.

Strokes may be diagnosed through several techniques, including a neurological examination, CT scans, MRI scans, Doppler ultrasound, and arteriography, among other techniques. Physical examinations may also be used to diagnose a stroke, including examinations relating to the patient's level of consciousness, horizontal eye movement, visual field tests, facial palsy, movement of the limbs (e.g., motor arm tests, motor leg tests, etc.), limb ataxia, sensory tests (e.g., responsiveness to touches or pinpricks, etc.), language skills (e.g., describing a picture, reading sentences and identifying objects, etc.), and motor skills (e.g., ability to speak coherently, including motor control of the tongue, lips, throat, and lungs), among others. Other signs of a stroke include, for example, slurred speech, new onset of weakness in arm or leg (most commonly in one side of body), and a degraded ability to walk. Such physiological characteristics are detectable using sensors and other monitoring devices and technologies, such as microphones, cameras (e.g., video cameras, infrared cameras, etc.), scanning devices, sonar, radar, motion sensors, pressure sensors (e.g., to measure blood pressure, etc.), and thermometers, among others.

As discussed in further detail in relation to the various embodiments disclosed herein, a stroke detection device may determine whether a patient experiences a stroke, including an embolic stroke, or the likelihood that the patient experienced an embolic stroke, based on whether the patient experienced atrial fibrillation at some time before or during the stroke. Several factors may be considered in making such a determination, including whether the patient experienced atrial fibrillation before stroking, features of the atrial fibrillation episode that the patient experiences (e.g., magnitude, duration, number of episodes, etc.), a duration between experiencing atrial fibrillation and stroking or duration after experiencing atrial fibrillation and stroking, and so on. Other factors and determinations may also be used in determining the likelihood of whether a patient experienced an embolic stroke, such as the patient's $CHADS_2$ score (i.e., a clinical prediction tool used to estimate the risk of stroke in patients based on other medical conditions), $CHA_2DS_2$-$VAS_C$ score (a variation of the $CHADS_2$ scoring methodology that includes additional stroke risk factors), and other medical history.

Referring now to FIG. 1, an illustration of home system 100 for detecting a stroke is shown, according to one embodiment. System 100 may include various devices, including furniture-mounted device 112, wearable device 114, and wall-or-ceiling-mounted device 116. In some embodiments, system 100 includes multiple devices, such as furniture-mounted device 112, wearable device 114 worn by patient 110, wall-or-ceiling-mounted device 116, and other devices, although system 100 may include a single device, such as wearable device 114. The devices may be configured to monitor patient 110. For example, the devices may be configured to monitor the heart rhythm or physiological characteristics of patient 110 to detect when patient 110 experiences a stroke, if patient 110 has already had a stroke, the likelihood that patient 110 will have a stroke, and so on, as will be discussed in further detail below. In multiple-device systems, the devices may communicate with one another, be configured to operate together, or be configured to operate independently of one another. Furniture-mounted device 112 may be configured to be affixed to furniture or other objects, such as appliances, toys, equipment, or other household items (e.g., vacuum cleaners, pets, robots, laundry baskets, etc.). As will be discussed in further detail below, the devices may be configured to communicate with systems or devices not shown or described in FIG. 1, such as emergency medical systems, medical providers, health monitoring stations, mobile devices, cellular systems, computer networks, communication networks, devices associated with a family member or emergency contact, among others.

Figure 2:
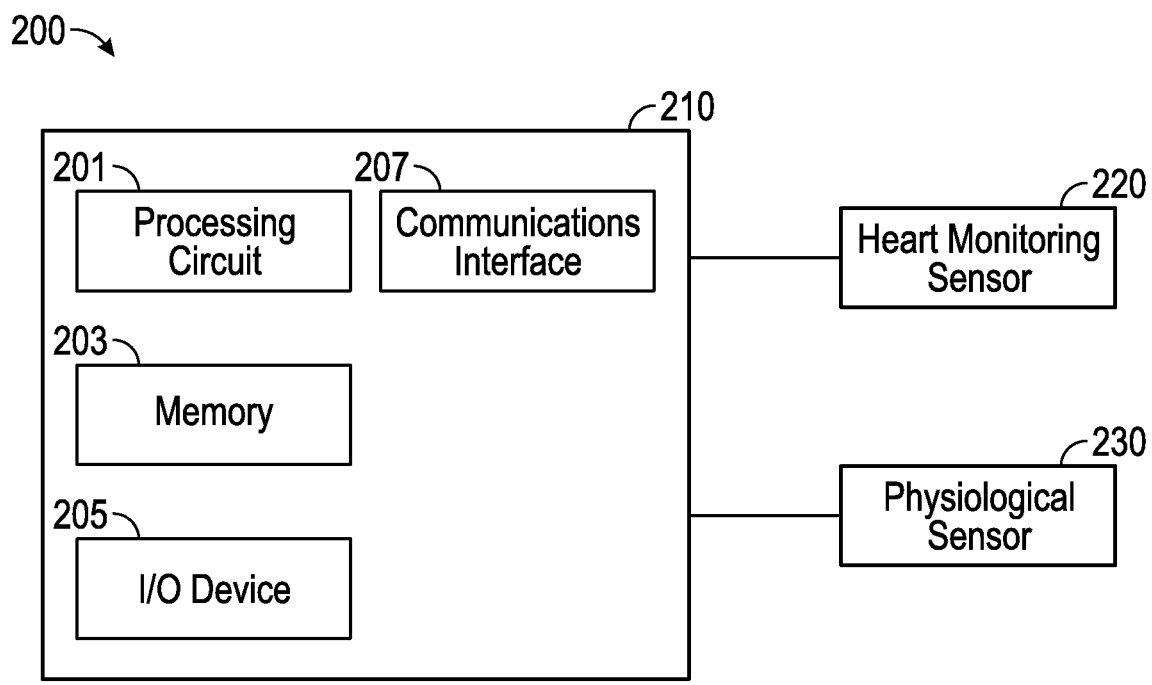
FIG. 2 is an illustration of a system for detecting a stroke, according to one embodiment.

Referring to FIG. 2, an illustration of system 200 for detecting a stroke is shown according to one embodiment. System 200 may include patient monitoring sensor, such as stroke detection device 210, heart-monitoring sensor 220, and physiological sensor 230. Devices used in home system 100, including furniture mounted device 112, wearable device 114, and wall-or-ceiling-mounted device 116, may be the same as or similar to system 200, or include components thereof, such as stroke detection device 210. System 200 may include any number of stroke detection devices 210, heart-monitoring sensors 220, and physiological sensors 230, as well as other elements not pictured in FIG. 2. Stroke detection device 210 may receive inputs from heart-monitoring sensor 220 and physiological sensor 230. For example, in some embodiments, stroke detection device 210 receives heart data from heart-monitoring sensor 220 and/or physiological data from physiological sensor 230. The heart data may include information relating to a heart rhythm of patient 110. For example, the heart data may be indicative of the fibrillation of the heart of patient 110, including whether patient 110 experiences atrial fibrillation. The physiological data may include information relating to a physiological characteristic of patient 110, including whether a physiological characteristic of patient 110 changes or otherwise indicates that patient 110 experiences a stroke. In some embodiments, sensors of system 200, such as physiological sensor 230 and heart-monitoring sensor 220, may be configured to continuously operate or monitor patient 110 or intermittently operate or monitor patient 110. For example, heart-monitoring sensor 220 may be included in system 100 (e.g., wall-or-ceiling-mounted device 116) and may remotely monitor patient 110 using micro-impulse radar. In some embodiments, sensors of system 200 may "sleep" or operate in a passive mode and may become active upon receiving an input (e.g., from processing circuit 201). For example, in one embodiment, processing circuit 201 may cause physiological sensor 230 to become activated based on determining that patient 110 is at a high risk of experiencing a stroke. In another example, processing circuit 201 may cause physiological sensor 230 to acquire data more frequently based on, for example, determining that patient 110 is at a high risk of stroking or has exceeded a stroke probability threshold. In an embodiment, processing circuit 201 may receive input from heart-monitoring sensor 220 indicative of an atrial fibrillation event and determine, responsive to receiving the input indicative of an atrial fibrillation event, that the patient's risk of stroking has increased or has exceeded a stroke probability threshold. In some embodiments, the stroke probability threshold may be based on a predetermined likelihood. The stroke probability threshold may be based on a determined likelihood, a learned likelihood, or a likelihood selected by patient 110. In some embodiments, system 200 may provide an output or otherwise communicate with another system (e.g., emergency service provider system, medical provider, the patient, etc.) based on determining that patient 110 is at a high risk of stroking or has exceeded a stroke likelihood threshold.

In some embodiments, stroke detection device 210 includes processing circuit 201, memory 203, input/output device 205, and communications interface 207. Processing circuit 201 may be implemented as one or more microprocessing elements, digital signal processing elements, application specific integrated circuit (ASIC) elements, field programmable gate array (FPGA) elements, groups of processing components, intellectual property cores, or other suitable electronic processing components configured on a single integrated circuit or on multiple integrated circuits. Memory 203 may be one or more devices (e.g., RAM, ROM, Flash memory, hard disk storage, etc.) for storing data and/or computer code for completing and/or facilitating the various processes described herein. Memory 203 may be or include non-transient volatile memory, non-volatile memory, and non-transitory computer storage media. Memory 203 may include data base components, object code components, script components, or any other type of information structure for supporting the various activities and information structures described herein. Memory 203 may be communicably connected to one or more processors and include computer code or instructions for executing one or more processes described herein.

Processing circuit 201 may be configured to receive data, make determinations, and provide outputs, according to some embodiments. Processing circuit 201 may be configured to receive heart data and physiological data, for example, from heart-monitoring sensor 220 and physiological sensor 230, or via a report from a human observing the patient. The received heart data may regard a heart rhythm of patient 110. The heart data may further be indicative of an occurrence of atrial fibrillation. For example, the heart data may include information regarding the magnitude and duration of heart fibrillation of patient 110. The received physiological data may regard a physiological characteristic of patient 110. The received physiological data may be indicative of an occurrence of a stroke. The received physiological data may be indicative of a time associated with a stroke, such as the time at which the data was collected or delivered, the time the stroke occurred, or the time at which the stroke was detected. For example, the physiological data may include information relating to cranial blood pressure of patient 110.

In some embodiments, processing circuit 201 is configured to determine a likelihood that a stroke was an embolic stroke. Processing circuit 201 may determine the likelihood based on received heart data, based on received physiological data, based on both the received heart data and the receive physiological data, and so on. In some embodiments, processing circuit 201 may determine whether patient 110 experiences or experienced atrial fibrillation. For example, processing circuit 201 may determine if patient 110 is experiencing atrial fibrillation based on a monitored heart rhythm (e.g., beats per minute, duration between beats, magnitude of fibrillation, etc.). Processing circuit 201 may determine whether patient 110 experienced an embolic stroke based on other factors as well, including whether patient 110 experienced a stroke and atrial fibrillation within a predetermined time period. For example, because a person may be more likely to experience an embolic stroke within three hours after experiencing atrial fibrillation, processing circuit 201 may determine that patient 110 likely experienced an embolic stroke based on determining that patient 110 experienced a stroke within three hours of experiencing atrial fibrillation. In some embodiments, the time period may be greater than or less than three hours (e.g., eight hours, overnight, until the following day, until a visit with a medical provider such as a doctor, etc.). In some embodiments, the time period may be based on the condition of patient 110, including a condition monitored by physiological sensor 230, or a fibrillation feature monitored by heart-monitoring sensor 220. In some embodiments, processing circuit 201 may be configured to operate differently depending on the likelihood of patient 110 experiencing a stroke.

For example, processing circuit 201 may be configured to treat a fall followed by inactivity as a likely stroke indicator, and may weigh such factors differently depending on the likelihood of patient 110 experiencing a stroke (e.g., following an atrial fibrillation event).

In some embodiments, processing circuit 201 is configured to provide an output. Processing circuit 201 may be configured to provide an output indicating whether patient 110 experienced a stroke. In some embodiments, processing circuit 201 is configured to control operation of stroke detection device 210 to provide an output. In some embodiments, the output is based on the likelihood that the stroke was an embolic stroke. In some embodiments, the output is based on a determination of whether patient 110 experienced an embolic stroke. In some embodiments, the output is based on a monitored physiological characteristic or heart data (e.g., via physiological sensor 230 and heart-monitoring sensor 220, respectively). For example, the output may be based on whether patient 110 experienced atrial fibrillation (e.g., providing a warning that patient 110 is at a heightened risk of experiencing a stroke, and/or that such a stroke has a higher likelihood of being an embolic stroke than a hemorrhagic stroke).

Processing circuit 201 may be configured to control various components of stroke detection device 210 or stroke detection system 200. For example, in some embodiments, physiological sensor 230 is configured to activate only upon receiving instructions from processing circuit 201 to activate. For example, in one embodiment, processing circuit 201 may cause physiological sensor 230 to become activated based on determining that patient 110 has a certain risk, probability, or likelihood of experiencing a stroke (e.g., following an atrial fibrillation event). In an embodiment, processing circuit 201 may cause physiological sensor 230 to provide data more frequently, or may analyze data more frequently, based on determining that patient 110 has a certain risk, probability, or likelihood of experiencing a stroke. In an embodiment, processing circuit 201 may change one or more parameters of a stroke determination algorithm (e.g., increasing the likelihood that an event such as a fall, a lack of motion, or slurred speech will be considered indicative of a stroke) based on determining that patient 110 has a certain risk, probability, or likelihood of experiencing a stroke.

Input/output device 205 may include devices to receive inputs or information (e.g., buttons, keyboard, touchscreen, microphones, etc.) or devices to provide outputs or information (e.g., speakers, display screen, lights, etc.). Input/output device 205 may be external from stroke detection device 210, such as a mobile device, stereo system, television, computer, tablet computer, personal digital assistant ("PDA"), watch, etc. In some embodiments, stroke detection device 210 may not include input/output device 205. When utilized with input/output device 205, stroke detection device 210 may receive input from input/output device 205 via communications interface 207 including, or in addition to, using a USB cable, Bluetooth technology, wireless technology, etc.

In some embodiments, in addition to the inputs described above, processing circuit 201 may receive inputs via input/output device 205. For example, processing circuit 201 may receive an input from input/output device 205 to selectively activate or deactivate processing circuit 201. Input/output device 205 may be configured to receive inputs from patient 110, or other operator, to control settings of stroke detection device 210. Such settings may include, for example, high-alert or low-alert monitoring time periods. For example, patient 110 may selectively configure stroke detection device 210 using input/output device 205 to set an inactive period (e.g., when patient 110 plans to be sleeping) in which stroke detection device 210 monitors patient 110 at less frequent intervals. In another example, patient 110 may selectively configure stroke detection device 210 using input/output device 205 to set a period of increased activity (e.g., when patient 110 plans to be sleeping) in which stroke detection device 210 monitors patient 110 at more frequent intervals.

Stroke detection device 210 is shown to include communications interface 207. Communications interface 207 may include wired or wireless interfaces (e.g., jacks, antennas, transmitters, receivers, transceivers, wire terminals, etc.) for conducting data communications with various systems, devices, or networks. For example, communications interface 207 may include an Ethernet card and port for sending and receiving data via an Ethernet-based communications network and/or a Wi-Fi transceiver for communicating via a wireless communications network. Communications interface 207 may be configured to communicate via local area networks or wide area networks (e.g., the Internet, a building WAN, etc.) and may use a variety of communications protocols (e.g., BACnet, IP, LON, etc.).

Communications interface 207 may be a network interface configured to facilitate electronic data communications between stroke detection device 210 and various external systems or devices (e.g., heart-monitoring sensor 220, physiological sensor 230, third-party medical provider systems, medical monitoring service devices, etc.). For example, stroke detection device 210 may send information to a medical provider system indicating that patient 110 has experienced atrial fibrillation and has a certain likelihood of experiencing a stroke during a period of time. Stroke detection device 210 may receive inputs from medical monitoring devices, emergency medical provider service systems, and sensors (e.g., heart-monitoring sensor 220, physiological sensor 230, etc.) via communications interface 207 and stroke detection device 210 may provide inputs or control devices via communications interface 207.

Heart-monitoring sensor 220 may include various types of sensors that are configured to monitor the heart or a heart rhythm of patient 110. For example, heart-monitoring sensor 220 may include, or monitor a heart rhythm using, an electrocardiogram (i.e., ECG or EKG) or ultra wideband radar (e.g., micro-impulse radar). For example, micro-impulse radar may be used to monitor a heart by bouncing radar off of a moving heart (i.e., beating heart), thereby monitoring the heart's motion. In some embodiments, heart-monitoring sensor 220 may be worn by patient 110, as will be further described below. For example, patient 110 may wear an electrocardiogram positioned over the heart (e.g., using a chest band, harness, halter monitor, etc.). Heart-monitoring sensor 220 may include a single electrode or a plurality of electrodes, which may be placed at various locations on patient 110 (e.g., over or near heart, on chest, arms, legs, etc.). Heart-monitoring sensor 220 may also monitor a heart rhythm using hemodynamic monitoring, which monitors the pressure and flow of blood within the circulatory system. In some embodiments, heart-monitoring sensor 220 is not worn by patient 110. For example, heart-monitoring sensor 220 may include a single sensor or a plurality of sensors placed in proximity to patient 110 (e.g., installed on a ceiling or wall, built-in or attached to an appliance, placed on a table, attached to a table, chair, bed, etc.).

Physiological sensor 230 may include various types of sensors that are configured to monitor a physiological characteristic of patient 110. Physiological sensor 230 may include microphones, cameras (e.g., video cameras, infrared cameras, etc.), keyboards (e.g., to detect typed phrases or ability to type), scanning devices, sonar, radar, motion sensors, pressure sensors (e.g., to measure blood pressure, etc.), thermometers, MRI devices, Doppler devices, eye tracking devices, among others. For example, microphones may monitor the language skills or motor skills of patient 110. Cameras may monitor the level of consciousness of patient 110 (e.g., by detecting the orientation of patient 110, detecting a fall, etc.). Physiological sensor 230 may be configured to detect, monitor, or otherwise acquire inputs relating to diagnosing, determining, or processing whether patient 110 has experienced a stroke, is currently experiencing a stroke, or may experience a stroke, including sensors configured to detect characteristics of patient 110 that may be indicative of a stroke, such as the level of consciousness, horizontal eye movement, visual field tests, facial palsy, movement of the limbs, limb ataxia, sensory tests, language skills, and motor skills, other physical and non-physical characteristics of patient 110, and so on. For example, in one embodiment, physiological sensor 230 may include a microphone configured to monitor speech patterns of patient 110. In another example, physiological sensor 230 may include a pressure sensor configured to monitor the cranial pressure of patient 110, including cranial blood pressure, or blood pressure of patient 110 elsewhere in the body. Physiological sensor 230 may include sensors configured to detect characteristics of patient 110 using CT scans, MRI scans, Doppler ultrasound, and arteriography, among other techniques.

Referring to FIGS. 3A-3C, illustrations of a wearable stroke detection device 310 are shown according to some embodiments. Stroke detection device 310 may be similar to or the same as stroke detection device 210, as described above. Stroke detection device 310 may include elements in addition to those described above with reference to stroke detection device 210, for example to enable wearability or enhance mobility. For example, stroke detection device 310 may include wristbands, straps, Velcro, clips, fasteners, etc. so that stroke detection device 310 may be worn by or carried by patient 110. In some embodiments, stroke detection device 310 may communicate with other devices, such as those shown in FIG. 1, including furniture mounted device 112 and wall-or-ceiling-mounted device 116. In some embodiments, stroke detection device 310 may be the same as or similar to wearable device 114.

As shown in FIG. 3A, in one embodiment stroke detection device 310 is configured to be fastened to the wrist of patient 110. In this embodiment, stroke detection device 310 may resemble a watch. Stroke detection device 310 may communicate (e.g., via communications interface 207) with a sensor, such as heart-monitoring sensor 320, or a plurality of sensors to, for example, receive inputs relating to a heartbeat rhythm of patient 110. For example, in one embodiment, heart-monitoring sensor 320 is affixed over the heart of patient 110 and sends input data to stroke detection device 310 using Bluetooth technology. In some embodiments, heart-monitoring sensor 320 may be the same as heart-monitoring sensor 220. In some embodiments, stroke detection device 310 may further include a physiological sensor, such as physiological sensor 230, as described above.

As shown in FIG. 3B, in one embodiment stroke detection device 310 is configured to be carried by patient 110. In this embodiment, stroke detection device 310 may resemble a mobile device, PDA, tablet computer, etc. Stroke detection device 310 may communicate (e.g., via communications interface 207) with a sensor, such as heart-monitoring sensor 320, or a plurality of sensors to, for example, receive inputs relating to a heartbeat rhythm of patient 110. For example, in one embodiment, heart-monitoring sensor 320 is worn as an arm-band over an arm of patient 110 and communicates with stroke detection device 310 using a cord. In some embodiments, stroke detection device 310 may further include a physiological sensor, such as physiological sensor 230, as described above.

As shown in FIG. 3C, in one embodiment stroke detection device 310 is configured to be worn by patient 110 (e.g., over a torso, etc.). In this embodiment, stroke detection device 310 may include heart-monitoring sensor 320. Stroke detection device 310 may communicate (e.g., via communications interface 207) with heart-monitoring sensor 320 and physiological sensor 330 to, for example, receive inputs relating to a heartbeat rhythm or a physiological characteristic of patient 110. For example, in one embodiment, stroke detection device 310 is worn as a chest wrap and communicates with physiological sensor 330 using a wireless communications technology. In some embodiments, physiological sensor 330 may be the same as physiological sensor 230. In some embodiments, physiological sensor 330 may be selectively activated and/or equipped by patient 110. For example, upon receiving an indication from stroke detection device 310 that patient 110 experienced atrial fibrillation, patient 110 may equip or activate physiological sensor 330. In some embodiments, patient 110 may be instructed to equip or activate physiological sensor 330, or processing circuit 201 may automatically equip or activate physiological sensor 330 if processing circuit 201 determines that the risk of patient 110 experiencing a stroke has exceeded a threshold value. For example, in one embodiment, upon processing circuit 201 determining that patient 110 has a 40% likelihood of experiencing a stroke within the next four hours based on the patient experiencing atrial fibrillation, processing circuit 201 automatically activates physiological sensor 330.

Figure 4:
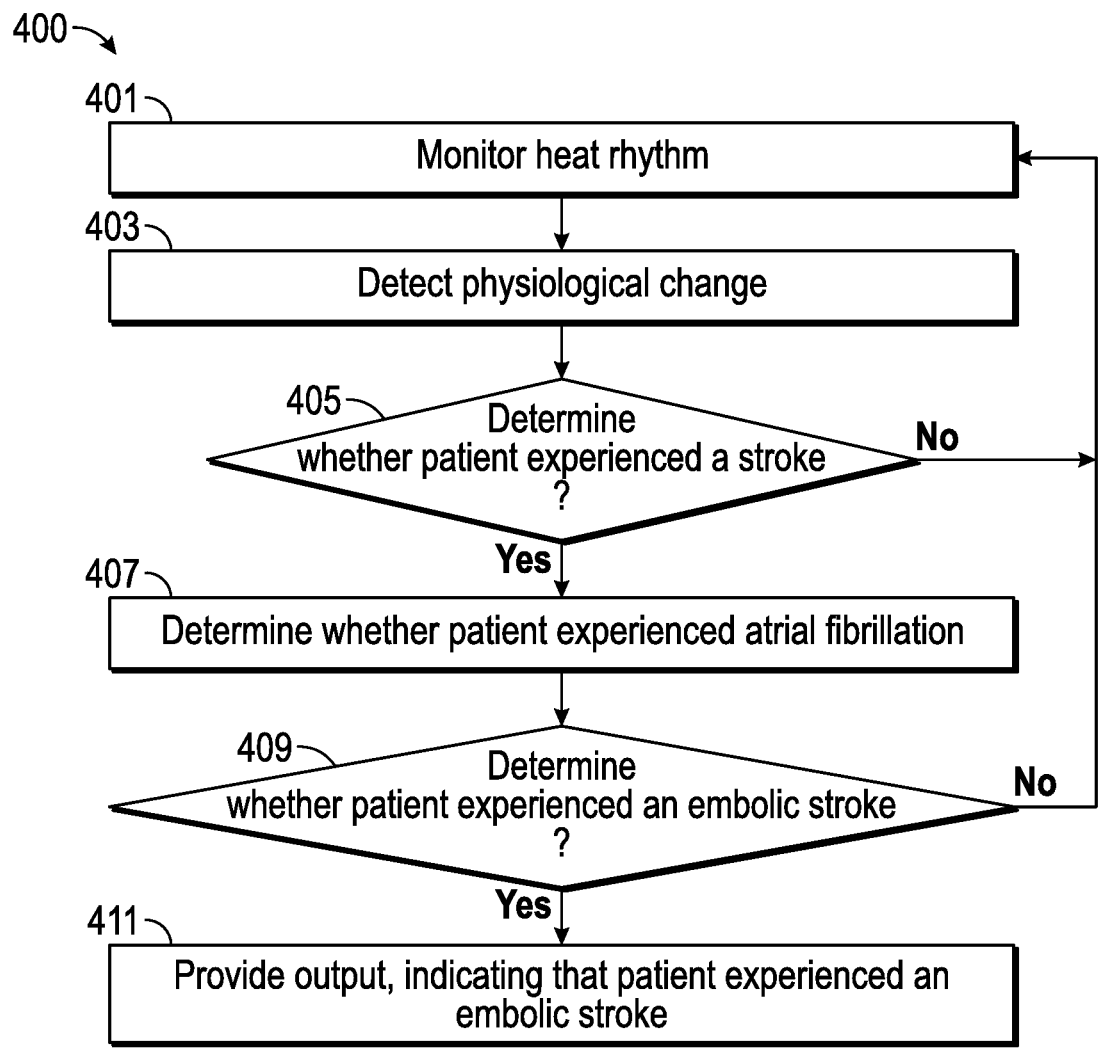
FIG. 4 is a diagram of a method for detecting a stroke, according to one embodiment.

Referring to FIG. 4, a block diagram of method 400 for detecting a stroke is shown according to one embodiment. According to one embodiment, method 400 is a computer-implemented method utilizing system 200 and/or device 210 or any of the other devices disclosed herein. For example, method 400 may utilize any of the devices included in home system 100, including furniture mounted device 112, wearable device 114, and wall-or-ceiling-mounted device 116. Method 400 may be implemented using any combination of computer hardware and software. According to one embodiment, the heart rhythm of a patient is monitored (401). For example, heart-monitoring sensor 220 may monitor the heart rhythm of patient 110. Next, a physiological change of the patient is detected (403). For example, physiological sensor 230 may detect a physiological change in patient 110, such as a physiological change that is indicative of a stroke, for example, slurred speech, falling down, change in consciousness, change in cranial blood pressure, and so on. Next, a determination is made as to whether the patient experienced a stroke (405). For example, determining whether the patient experienced a stroke may be based on the physiological change detected in step 403. If it is determined that patient 110 has not experienced a stroke, then method 400 returns to monitoring the heart rhythm of patient 110 in step 401. Next, a determination is made as to whether patient 110 experienced atrial fibrillation (407) (e.g., via heart data acquired by heart-monitoring sensor 220). For example, wall-or-ceiling-mounted device 116 may be configured to acquire heart data using micro-impulse radar. Next, a determination is made as to whether patient 110 likely experienced an embolic stroke (409). For example, processing circuit 201 may determine that patient 110 experienced an embolic stroke based on patient 110 experiencing atrial fibrillation within five hours of experiencing a stroke, and based on the magnitude and duration of the fibrillation (i.e., processing circuit 201 may determine that the fact the atrial fibrillation occurred increases the likelihood that a subsequently occurring stroke is an embolic stroke rather than a hemorrhagic stroke). If it is determined that patient 110 has not experienced a stroke, then method 400 returns to monitoring the heart rhythm of patient 110 in step 401. If it is determined that patient 110 likely experienced an embolic stroke at step 409, then an output is provided that indicates that patient 110 experienced an embolic stroke (411). In some embodiments, an output may still be provided that patient 110 experienced a stroke even if the stroke is not an embolic stroke. It will be appreciated that the order of the steps may vary, with steps occurring in a different order than that which they are discussed or as shown in the Figures. For example, in some embodiments, step 407 may occur between steps 401 and 403.

Figure 5:
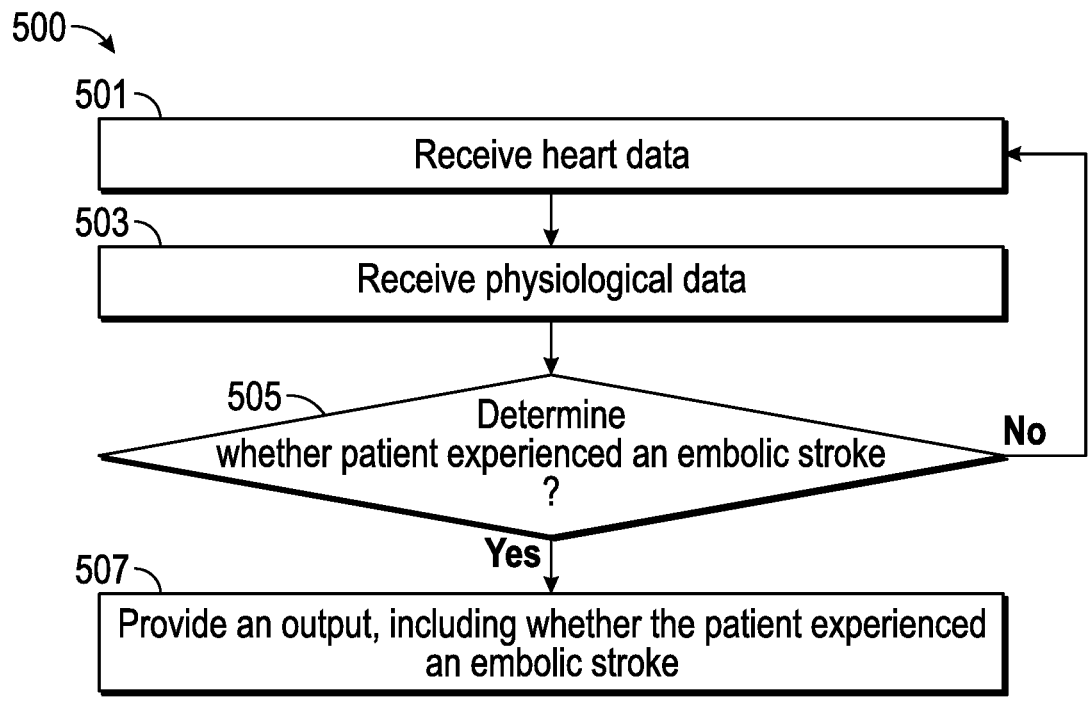
FIG. 5 is a diagram of a method for detecting a stroke, according to another embodiment.

Referring to FIG. 5, a block diagram of method 500 for detecting a stroke is shown according to another embodiment. According to one embodiment, method 500 is a computer-implemented method utilizing system 200 and/or device 210 or any of the other devices disclosed herein. For example, method 500 may utilize any of the devices included in home system 100, including furniture mounted device 112, wearable device 114, and wall-or-ceiling-mounted device 116. Method 500 may be implemented using any combination of computer hardware and software. According to one embodiment, heart data is received (501). For example, heart data may be received from heart-monitoring sensor 220. For example, wall-or-ceiling-mounted device 116 may be configured to acquire heart data using micro-impulse radar. The heart data may further regard a heart rhythm of patient 110. The heart data may be indicative of an occurrence of atrial fibrillation. Next, physiological data is received (503). For example, physiological data may be received from physiological sensor 230. The physiological data may regard a physiological characteristic of patient 110. The physiological data may be indicative of an occurrence of a stroke, for example, change in cranial blood pressure. Next, a determination is made as to whether the patient likely experienced an embolic stroke (505) (e.g., based on the physiological data and heart data). Next, an output is provided that includes whether patient 110 experienced an embolic stroke (507). For example, the output may include sounds, visual indicators, and/or may transmit to another device or system (e.g., an emergency medical provider). It will be appreciated that the order of the steps may vary, with steps occurring in a different order than that which they are discussed or as shown in the Figures.

Figure 6:
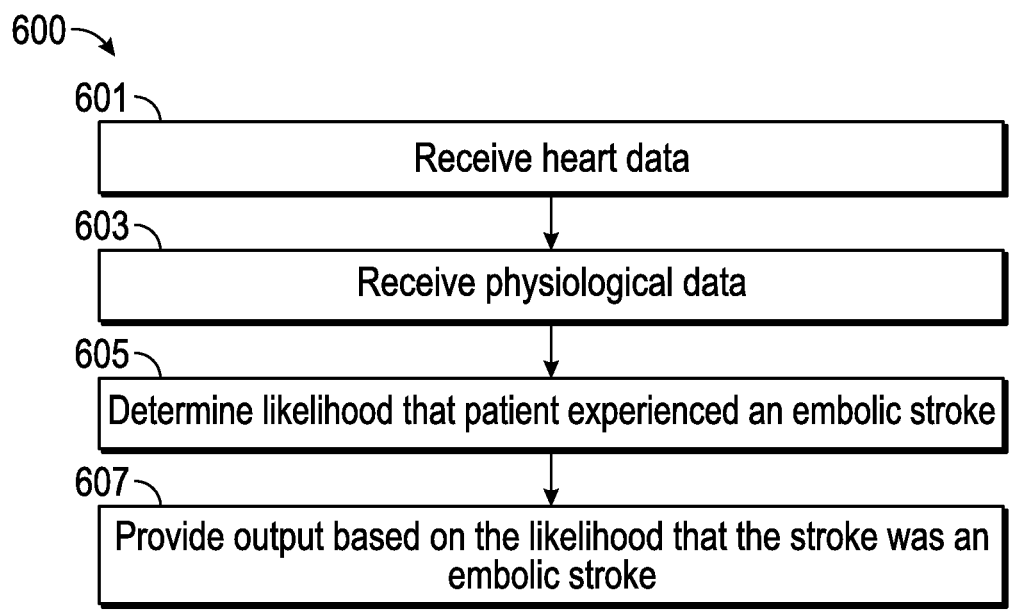
FIG. 6 is a diagram of a method for detecting a stroke, according to one embodiment.

Referring to FIG. 6, a block diagram of method 600 for detecting a stroke is shown according to one embodiment. According to one embodiment, method 600 is a computer-implemented method utilizing system 200 and/or device 210 or any of the other devices disclosed herein. For example, method 600 may utilize any of the devices included in home system 100, including furniture mounted device 112, wearable device 114, and wall-or-ceiling-mounted device 116. Method 600 may be implemented using any combination of computer hardware and software. According to one embodiment, heart data is received which is indicative of an occurrence of atrial fibrillation (601). For example, heart data may be received from heart-monitoring sensor 220. In one embodiment, furniture-mounted device 116 may be configured to acquire heart data using micro-impulse radar. Next, physiological data is received which is indicative of an occurrence of a stroke (603). For example, physiological data may be received from physiological sensor 230. Next, the likelihood that patient 110 experienced an embolic stroke is determined based on the heart data (605). For example, processing circuit 201 may determine that patient 110 experienced an embolic stroke based on patient 110 experiencing atrial fibrillation, falling down, and/or slurring their speech unlike their typical speaking pattern prior to experiencing atrial fibrillation and falling down. In some embodiments, an output may be provided based on the likelihood that the stroke was an embolic stroke (607). It will be appreciated that the order of the steps may vary, with steps occurring in a different order than that which they are discussed or as shown in the Figures.

Figure 7:
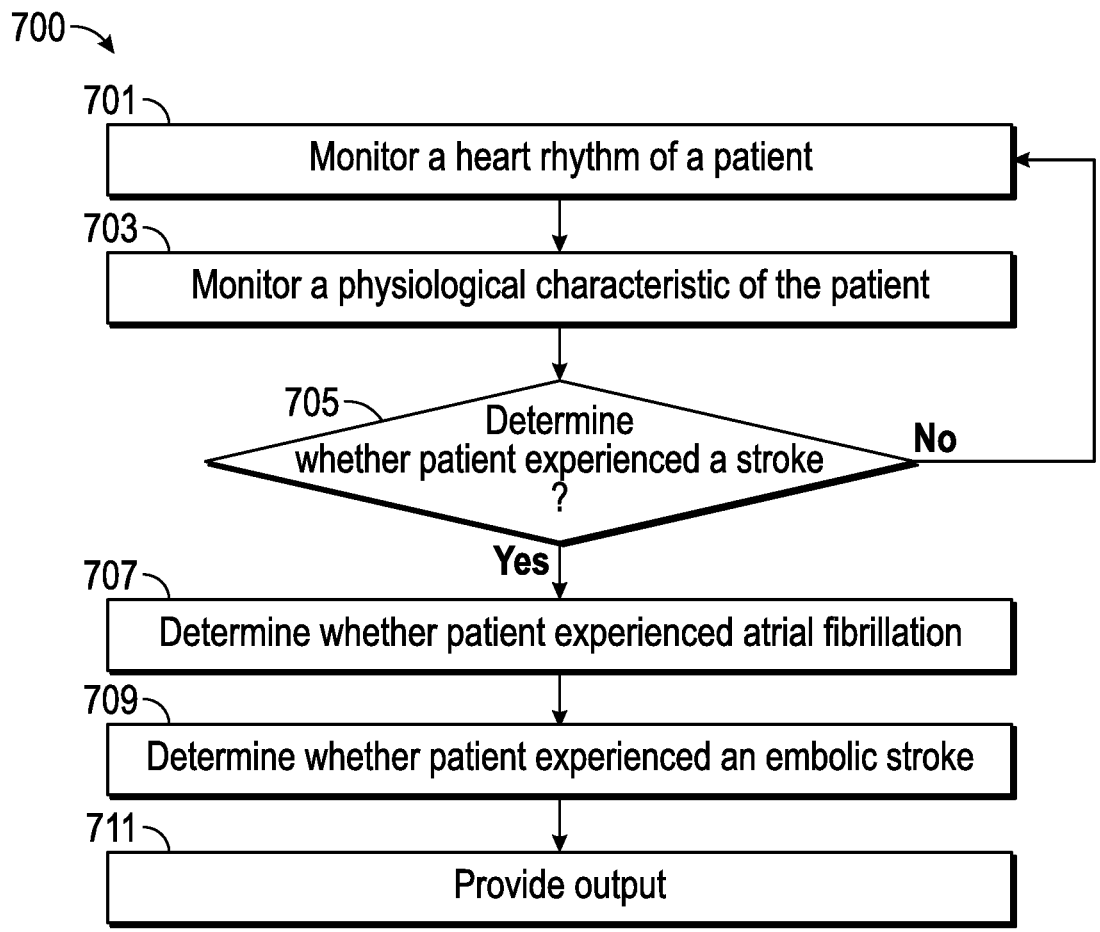
FIG. 7 is a diagram of a method for detecting a medical event, according to one embodiment.

Referring to FIG. 7, a block diagram of method 700 for detecting a medical event is shown according to one embodiment. According to one embodiment, method 700 is a computer-implemented method utilizing system 200 and/or device 210 or any of the other devices disclosed herein. For example, method 700 may utilize any of the devices included in home system 100, including furniture mounted device 112, wearable device 114, and wall-or-ceiling-mounted device 116. Method 700 may be implemented using any combination of computer hardware and software. According to one embodiment, a heart rhythm of a patient is monitored (701). For example, the heart rhythm of patient 110 may be monitored using heart-monitoring sensor 220. Next, a physiological characteristic of the patient is monitored (703). For example, the physiological characteristic may be monitored using physiological sensor 230. Next, a determination is made as to whether the patient experienced a stroke based on the monitored physiological characteristic (705). Next, a determination is made as to whether the patient experienced atrial fibrillation based on the monitored heart rhythm (707). Next, a determination is made as to whether the patient experienced an embolic stroke based on the patient experiencing a stroke and atrial fibrillation within a predetermined time period (709). For example, processing circuit 201 may determine that patient 110 experienced an embolic stroke if patient 110 experienced atrial fibrillation within one hour of experiencing a stroke. Next, an output is provided (711) based on the determination of whether the patient experienced an embolic stroke carried out in step 709. It will be appreciated that the order of the steps may vary, with steps occurring in a different order than that which they are discussed or as shown in the Figures. For example, in some embodiments, step 707 may occur between steps 701 and 703.

Figure 8:
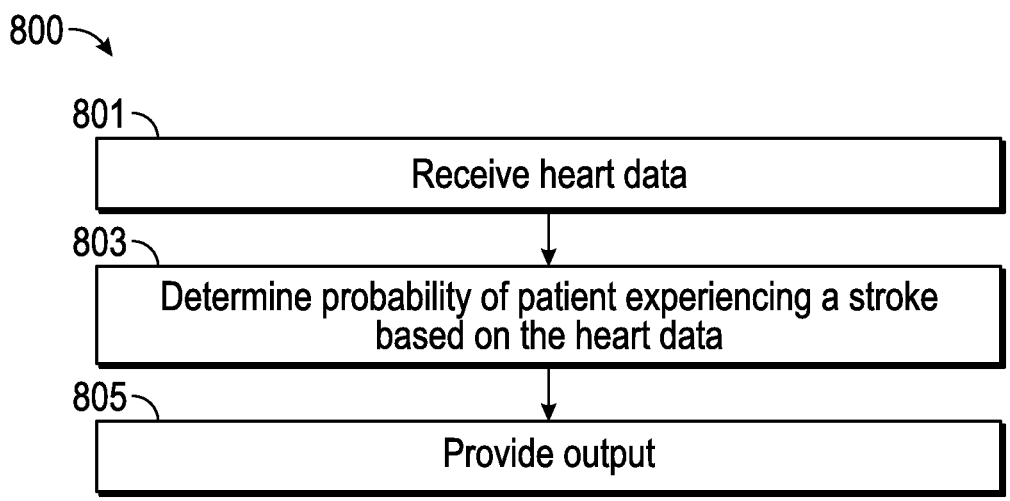
FIG. 8 is a diagram of a method for determining a probability of a patient experiencing a stroke, according to one embodiment.

Referring to FIG. 8, a block diagram of method 800 for determining a probability of a patient experiencing a stroke is shown according to one embodiment. According to one embodiment, method 800 is a computer-implemented method utilizing system 200 and/or device 210 or any other devices disclosed herein. For example, method 800 may utilize any of the devices included in home system 100, including furniture mounted device 112, wearable device 114, and wall-or-ceiling-mounted device 116. Method 800 may be implemented using any combination of computer hardware and software. According to one embodiment, heart data is received (801). For example, heart data may be received from heart-monitoring sensor 220. The heart data may be based on a monitored heart rhythm of patient 110. The heart data may be indicative of patient 110 experiencing atrial fibrillation. Next, a probability of the patient experiencing a future stroke is determined based on the heart data (803). For example, processing circuit 201 may determine that patient 110 has an 80% chance of experiencing a stroke within a one-hour time window, a 70% chance of experiencing a stroke within a two-hour time window, a 50% chance of experiencing a stoke within a three-hour time window, and less than a 25% chance of experiencing a stroke after four hours based on received heart data, including heart data indicative of atrial fibrillation, fibrillation magnitude, time between fibrillation magnitudes of a certain threshold, and so on. In some embodiments, an output may be provided (805) based on the probability of patient 110 experiencing a stroke. For example, a warning may be provided to patient 110 if patient 110 has a 50% or greater chance of experiencing a stroke at any given time.

The construction and arrangement of the systems, methods, and devices as shown in the various embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the embodiments without departing from the scope of the present disclosure.

The present disclosure contemplates methods, systems and program products on any machine-readable media for accomplishing various operations. The embodiments of the present disclosure may be implemented or modeled using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

Although the figures may show a specific order of method steps, the order of the steps may differ from what is depicted. Also two or more steps may be performed concurrently or with partial concurrence. All such variations are within the scope of the disclosure. Likewise, software implementations could be accomplished with standard programming techniques with rule-based logic and other logic to accomplish the various connection steps, processing steps, comparison steps and decision steps.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

What is claimed is:

1. A system for detecting a type of stroke, comprising:
a heart-monitoring device configured to acquire heart data regarding a heart rhythm of a patient,
and
wherein the heart-monitoring device acquires heart data using micro impulse radar; and
a processing circuit configured to:
receive the heart data and determine an occurrence of atrial fibrillation based on the heart data;
receive physiological data regarding a physiological characteristic of the patient and determine an occurrence of a stroke based on the physiological data,
determine that the stroke was an embolic stroke based on whether the atrial fibrillation and the stroke occurred within a predetermined time period; and
control operation of a computing device to provide an output based on the determination that the stroke was an embolic stroke,
wherein the output comprising at least one of a sound, a visual indicator, and information regarding the stroke experienced by the patient transmitted to a device.

2. The system of claim 1, further comprising a patient-monitoring sensor, wherein the patient-monitoring sensor is remote from the patient.

3. The system of claim 2, wherein the patient-monitoring sensor is configured to acquire the physiological data using micro impulse radar.

4. The system of claim 2, wherein the patient-monitoring sensor is configured to acquire the physiological data using a camera.

5. The system of claim 2, wherein the patient-monitoring sensor is configured to acquire the physiological data using a microphone.

6. The system of claim 1, wherein the heart-monitoring device comprises a wearable heart-monitoring device configured to acquire the heart data.

7. The system of claim 6, wherein the wearable heart-monitoring device further comprises an electrocardiogram (EKG) monitor.

8. The system of claim 1, wherein the processing circuit is further configured to determine a probability of the patient's heart emitting an embolus based on the heart data.

9. The system of claim 1, wherein determining that the stroke was an embolic stroke is further based on a probability of the patient's heart emitting an embolus, wherein the probability of the patient's heart emitting the embolus is determined based on the heart data.

10. The system of claim 7, wherein the heart data provides an indication of a fibrillation feature of the atrial fibrillation.

11. The system of claim 10, wherein the fibrillation feature provides an indication of at least one of a magnitude of the fibrillation, a duration of the fibrillation, and a number of episodes of fibrillation.

12. The system of claim 1, wherein the processing circuit is further configured to control operation of the computing device to provide the output to at least one of the patient and a medical provider.

13. The system of claim 1, wherein the hear-monitoring device is further configured to be accessed by a medical provider.

14. The system of claim 1, wherein the output includes at least one of an audible output, tactile output, and a visual output.

15. A system for detecting a type of stroke, comprising:
a heart-monitoring device configured to acquire heart data regarding a heart rhythm of a patient,
wherein the heart-monitoring device acquires heart data using micro impulse radar, and
wherein the heart-monitoring device comprises a physiological sensor configured to monitor a physiological characteristic of the patient,
wherein monitoring the physiological characteristic includes acquiring physiological data; and
a processing circuit configured to:
receive the heart data and determine an occurrence of atrial fibrillation based on the heart data;
receive the physiological data and determine an occurrence of a stroke based on the physiological data,
determine that the stroke was an embolic stroke based on whether the atrial fibrillation and the stroke occurred within a predetermined time period; and
control operation of a computing device to provide an output based on the determination that the stroke was an embolic stroke, the output comprising at least one of a sound, a visual indicator, and information regarding the stroke experienced by the patient transmitted to a device.

16. The system of claim 15, wherein the physiological data is based on an audio signal received from the patient.

17. The system of claim 15, wherein the physiological data comprises a time associated with the occurrence of the stroke.

18. The system of claim 17, wherein the time includes a start time of the stroke.

19. The system of claim 17, wherein the time includes a collection time of the physiological data.

20. The system of claim 17, wherein the time includes a time of the diagnosis that a stroke occurred.

21. The system of claim 15, wherein the physiological data is based on a lack of motion of the patient.

22. The system of claim 15, wherein the physiological data includes an indication of a change in the patient's orientation.

23. The system of claim 15, wherein the physiological data includes an indication of a change in the patient's cranial pressure.

24. The system of claim 15, wherein the physiological data includes an indication of a change in the patient's speech.

* * * * *